United States Patent
Hähnle et al.

(10) Patent No.: US 6,455,600 B1
(45) Date of Patent: Sep. 24, 2002

(54) WATER-ABSORBING, CROSS-LINKED POLYMERIZATES IN THE FORM OF A FOAM, A METHOD FOR THE PRODUCTION THEREOF, AND THEIR USE

(75) Inventors: Hans-Joachim Hähnle, Neustadt; Ulrich Schröder, Frankenthal; Martin Beck, Freinsheim; Wolfgang Heider, Neustadt; Gunnar Schornick, Neuleiningen; Thomas Anstock, Weisenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/623,590

(22) PCT Filed: Mar. 3, 1999

(86) PCT No.: PCT/EP99/01363
§ 371 (c)(1),
(2), (4) Date: Sep. 5, 2000

(87) PCT Pub. No.: WO99/44648
PCT Pub. Date: Sep. 10, 1999

(30) Foreign Application Priority Data

Mar. 5, 1998 (DE) ......................................... 198 09 540

(51) Int. Cl.$^7$ ................................................. C08J 9/28
(52) U.S. Cl. ............................................ 521/63; 521/64
(58) Field of Search ..................................... 521/63, 64

(56) References Cited

U.S. PATENT DOCUMENTS

| | | |
|---|---|---|
| 4,394,930 A | 7/1983 | Korpman |
| 4,415,388 A | 11/1983 | Korpman |
| 4,529,739 A | 7/1985 | Scott et al. |
| 4,649,154 A | 3/1987 | Dolman et al. |
| 4,725,628 A | 2/1988 | Garvey et al. |
| 4,725,629 A | 2/1988 | Garvey et al. |
| 4,731,391 A | 3/1988 | Garvey |
| 4,808,637 A | 2/1989 | Boardman et al. |
| 4,985,467 A | 1/1991 | Kelly et al. |
| 4,990,541 A | 2/1991 | Nielsen et al. |
| 5,182,312 A | 1/1993 | Engelhardt et al. |

FOREIGN PATENT DOCUMENTS

| | | |
|---|---|---|
| DE | 195 40 951 | 5/1997 |
| DE | 196 07 529 | 9/1997 |
| DE | 196 07 551 | 9/1997 |
| EP | 0 421 264 | 4/1991 |
| EP | 0 427 219 | 5/1991 |
| EP | 0 721 659 | 5/1996 |
| GB | 858478 | 1/1961 |
| GB | 2 136 813 | 9/1984 |
| JP | A-08073507 | * 3/1996 |
| WO | WO 88/09801 | 12/1988 |
| WO | WO 94/22502 | 10/1994 |
| WO | WO 95/02002 | 1/1995 |
| WO | WO 98/32602 | 7/1998 |

OTHER PUBLICATIONS

Chemical Abstracts, vol. 125, No. 4, Jul. 22, 1996, AN 35562, JP 08 073507, Mar. 19, 1996.

* cited by examiner

*Primary Examiner*—Morton Foelak
(74) *Attorney, Agent, or Firm*—Oblon, Spivak, McClelland, Maier & Neustadt, P.C.

(57) ABSTRACT

A water-absorbing, expanded, crosslinked polymer obtainable by (I) foaming a polymerizable aqueous mixture which comprises
  (a) monoethylenically unsaturated monomers which contain acidic groups and are optionally neutralized,
  (b) optionally other monoethylenically unsaturated monomers,
  (c) crosslinkers,
  (d) initiators,
  (e) 0.1–20% by weight of at least one surfactant,
  (f) optionally at least one solubilizer and
  (g) optionally thickeners, foam stabilizers, polymerization regulators, fillers and/or cell nucleating agents,
  where the foaming takes place by dispersing fine bubbles of a gas which is inert to free radicals in the polymerizable aqueous mixture, and (II) polymerizing the foamed mixture to form an expanded hydrogel, whereby at least 20 mol % of the monomers (a) which contain acidic groups have been neutralized with tertiary alkanolamines and/or the free acidic groups of the expanded hydrogel have been at least 20 mol % neutralized with at least one alkalolamine after the polymerization, and, where appropriate, adjusting the water content of the expanded polymer to 1–60% by weight, the production thereof and the use thereof in hygiene articles employed to absorb body fluids and in dressing material for covering wounds.

19 Claims, No Drawings

WATER-ABSORBING, CROSS-LINKED POLYMERIZATES IN THE FORM OF A FOAM, A METHOD FOR THE PRODUCTION THEREOF, AND THEIR USE

The invention relates to water-absorbing, expanded, crosslinked polymers, to a process for the production thereof and to the use thereof in hygiene articles employed to absorb body fluids and in dressing material for covering wounds.

Water-absorbing, crosslinked polymers are referred to as superabsorbents or superabsorbing polymers because they are able to absorb a multiple of their own weight of aqueous liquids to form hydrogels. Superabsorbents are used in practice, for example, in diapers for absorbing urine. The superabsorbents have the property of retaining the absorbed liquid even under mechanical stress.

In order to alter the use properties of superabsorbents, two different types of foams are known: (1) mixtures which contain superabsorbents in a foamed matrix, and (2) foams which consist of a superabsorbing material.

A foam belonging to category (1) is produced, for example, from a mixture which comprises, on the one hand, components for forming a polyurethane foam and, on the other hand, polymerizable monomers, a crosslinker and a polymerization initiator to produce a superabsorbent. The foam is formed from the polyurethane components in a mixture of this type in a polycondensation reaction and contains the superabsorbent which has been produced by polymerization of the monomers in the form of an interpenetrating network, cf. U.S. Pat. Nos. 4,725,628, 4,725,629 and 4,731,391.

U.S. Pat. No. 4,985,467 discloses a polyurethane foam which contains a chemically bonded superabsorbent. Also known are combinations of latex foams into which superabsorbing, fine-particle materials are incorporated after the foaming process, cf. EP-A-427 219 and U.S. Pat. No. 4,990,541.

Products belonging to category (2) of foams are those, for example, which are obtained by mixing a prefabricated superabsorbent in an extruder with a polyhydroxy compound and a blowing agent at elevated temperature. The foam is formed when the mixture is expelled from the extruder. Processes of this type are described, for example, in U.S. Pat. Nos. 4,394,930, 4,415,388 and GB-A-2 136 813.

U.S. Pat. Nos. 4,529,739 and 4,649,154 disclose processes for producing foams in which a water-swellable material having COOH groups is foamed with a blowing agent which liberates the blowing gas in a neutralization reaction with the COOH groups of the polymer.

According to the statements in WO-A 94/22502, superabsorbing foams based on crosslinked, partially neutralized polycarboxylates are produced by foaming a monomer mixture with a blowing agent which is insoluble in water and has a boiling point below 50° C., and completing polymerization of the foam at virtually the same time as the foaming.

EP-A-04 21 264 discloses the production of foam-like superabsorbents by polymerizing an aqueous monomer mixture which contains an emulsified oil phase. The action of the oil in this case is to occupy the space for the later pores in the foam and it is removed by evaporation, after the polymerization is complete, on drying the expanded material.

WO-A 88/09801 discloses that it is possible to process hydrophilic polymers, e.g. sodium polyacrylate, in the presence of crosslinkers such as polyepoxides and blowing agents, by heating, to an expanded superabsorbent.

Another procedure known for producing expanded superabsorbents is to add carbonates, bicarbonates or carbon dioxide as blowing agents to a mixture of monomers which contain carboxyl groups, crosslinker and polymerization initiator, with the polymerization of the monomers being started at the same time as the addition of the blowing agent or shortly thereafter. The superabsorbent acquires a foam structure due to the carbon dioxide formed in the neutralization reaction, cf. EP-A-2 954 438 and U.S. Pat. No. 4,808,637. In the process disclosed in WO-A 95/02002, an expanded superabsorbent is mixed after production with one or more reactive compounds for subsequent surface crosslinking, and is heated to from 100 to 300° C.

In the processes described above for producing superabsorbing foams, the foam formation and the polymerization take place either synchronously or at negligibly different times. The foams which have not yet completely polymerized have only a short pot life, usually only a few minutes. It is a disadvantage in the processes indicated above that, for example, relatively large amounts of blowing agent are used, especially the CFCs used in the case of WO-A 94/22502.

DE-A-19607551 discloses water-absorbing, expanded, crosslinked polymers which are obtainable by
(I) foaming a polymerizable aqueous mixture which comprises
   (a) monoethylenically unsaturated monomers which contain acidic groups and are at least 50 mol % neutralized,
   (b) optionally other monoethylenically unsaturated monomers,
   (c) crosslinkers,
   (d) initiators,
   (e) 0.1–20% by weight of at least one surfactant,
   (f) optionally at least one solubilizer and
   (g) optionally thickeners, foam stabilizers, polymerization regulators, fillers and/or cell nucleating agents
   where the foaming takes place by dispersing fine bubbles of a gas which is inert to free radicals in the polymerizable aqueous mixture, and
(II) polymerizing the foamed mixture to form an expanded hydrogel and, where appropriate, adjusting the water content of the polymer to 1–60% by weight.

According to the disclosure of DE-A-19540951, the water content of the expanded hydrogel is adjusted to 1–45% by weight. The expanded polymers obtainable in this way are used in hygiene articles, for example for absorbing body fluids.

JP-A-08073507 describes soft and flexible superabsorbent films which are produced by polymerizing an aqueous acrylate solution which is partly neutralized by an alkanolamine in the presence of a crosslinker. Although the resulting films are described as soft and flexible, no information is given on the climatic conditions under which the flexibility is retained. In particular, no information is available for elevated or reduced temperatures. In addition, these products have several serious disadvantages. Thus, their absorption speed is completely inadequate for use in hygiene articles, and their absorption capacity is also in need of improvement. Furthermore, the films show pronounced tackiness which greatly impairs handling.

Superabsorbent foams based on crosslinked polymers with acidic groups, which are produced, for example, as described in the abovementioned references DE-A-19540951, DE-A-19607551 or WO-A-94/22502 can be obtained in soft and flexible form by adjusting a defined moisture content of about 25%. Even if additional flexibilization measures as described in the above patents are taken, nevertheless a moisture content of at least 20% is usually necessary. Flexibilization by such a high water content entails the disadvantage that it is not stable at low humidities. At a relative humidity below 50%, the foam starts to dry out and thus increasingly loses its flexibility. Likewise, the flexibility of the foam decreases rapidly at temperatures below 5° C.

Although the loss of flexibility is reversible, i.e. when the temperature rises or the humidity increases the foams again become soft and flexible, nevertheless this represents a serious limitation on use, for example if a hygiene article is stored in very dry air at home. Furthermore, the resulting foam layers feel moist (moist "handle") which is likewise regarded as disadvantageous for use in hygiene articles.

It is an object of the present invention to provide a superabsorbing foam which remains flexible and, at the same time, overcomes the other disadvantages described under conditions relevant to use, for example at temperatures between −15° C. and +50° C. and a relative humidity of 20 to 95%.

We have found that this object is achieved by water-absorbing, expanded, crosslinked polymers obtainable by (I) foaming a polymerizable aqueous mixture which comprises
   (a) monoethylenically unsaturated monomers which contain acidic groups and are optionally neutralized,
   (b) optionally other monoethylenically unsaturated monomers,
   (c) crosslinkers,
   (d) initiators,
   (e) 0.1–20% by weight of at least one surfactant,
   (f) optionally at least one solubilizer and
   (g) optionally thickeners, foam stabilizers, polymerization regulators, fillers and/or cell nucleating agents,
   where the foaming takes place by dispersing fine bubbles of a gas which is inert to free radicals in the polymerizable aqueous mixture, and (II) polymerizing the foamed mixture to form an expanded hydrogel and, where appropriate, adjusting the water content of the expanded polymer to 1–60% by weight, if at least 20 mol % of the monomers (a) which contain acidic groups have been neutralized with tertiary alkanolamines and/or the free acidic groups of the expanded hydrogel have been at least 20 mol % neutralized with at least one alkanolamine after the polymerization.

The invention additionally relates to a process for producing water-absorbing, expanded, crosslinked polymers, which comprises foaming a polymerizable aqueous mixture of (a) monoethylenically unsaturated monomers which contain acidic groups and are optionally neutralized,
(b) optionally other monoethylenically unsaturated monomers,
(c) crosslinkers,
(d) initiators,
(e) 0.1–20% by weight of at least one surfactant,
(f) optionally at least one solubilizer and
(g) optionally thickeners, foam stabilizers, polymerization regulators, fillers and/or cell nucleating agents, in a first stage by dispersing fine bubbles of a gas which is inert to free radicals, and polymerizing the resulting foam in a second stage to form an expanded hydrogel, and, where appropriate, adjusting the water content of the expanded hydrogel to 1–60% by weight, wherein at least 20 mol % of the monomers (a) which contain acidic groups are neutralized with tertiary alkanolamines and/or the free acidic groups of the expanded hydrogel are at least 20 mol % neutralized with at least one alkanolamine after the polymerization.

This procedure not only results in flexible foams stable on storage in the abovementioned climatic zone but also distinctly improves their absorption speeds for body fluids. In addition, surprisingly, this measure increases the absorption capacity and also eliminates the problem of moist handle. The extreme tackiness can be solved by additional dusting with fine-particle hydrophilic powders. In addition, the present foam makes it possible for the alkanolamines to be applied subsequently, i.e. after the polymerization, e.g. by spraying. This is not practicable for the films described above because the times needed for absorption into the film are useless for practical application, and a homogeneous neutralization reaction cannot be achieved. The possibility of "subsequent neutralization" extends the range of alkanolamines which can be used to secondary and primary types. Addition of these two alkanolamine types to a monomer mixture as described in JP-A 08073507 is impossible because they undergo Michael addition reactions with acrylates.

A polymerizable aqueous mixture is processed according to the invention to a foam which is stable to processing and can be molded as required. The polymerizable aqueous mixture comprises as components (a) monoethylenically unsaturated monomers which contain acidic groups and which are, where appropriate, neutralized. Examples of monomers of this type are monoethylenically unsaturated $C_3$–$C_{25}$-carboxylic acids or anhydrides, for example acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid.

Also suitable as group (a) monomers are monoethylenically unsaturated sulfonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxypropylsulfonic acid, vinylphosphonic acid, allylphosphonic acid and 2-acrylamido-2-methylpropanesulfonic acid. The monomers can be used alone or mixed with one another to produce the superabsorbing foams. Group (a) monomers which are preferably used are acrylic acid, methacrylic acid, vinylsulfonic acid, acrylamidopropanesulfonic acid or mixtures of these acids, e.g. mixtures of acrylic acid and methacrylic acid, mixtures of acrylic acid and acrylamidopropanesulfonic acid or mixtures of acrylic acid and vinylsulfonic acid.

The monomers are neutralized, where appropriate. Alkali metal bases or ammonia or amines are used, for example, for the neutralization. Sodium hydroxide solution or potassium hydroxide solution is preferably used for the neutralization. However, the neutralization can also be carried out with sodium carbonate, sodium bicarbonate, potassium carbonate or potassium bicarbonate or other carbonates or bicarbonates or ammonia. The acidic groups in the monomers are preferably at least 15 to 40 mol % neutralized with at least one of the abovementioned bases.

In one embodiment of the process according to the invention the monomers (a) are at least 20 mol % neutralized with tertiary alkanolamines. A particularly preferred embodiment is one in which at least 40 mol % of the monomers (a) which contain acidic groups are neturalized with tertiary alkanolamines. In this embodiment of the process according to the invention the monomers (a) can, where appropriate, additionally be up to, for example, 100% neutralized with the bases described above, in particular NaOH or ammonia. The degree of neutralization of the monomers (a) which contain acidic groups with tertiary alkanolamines in this process variant is 20–95, preferably 30–70, mol %. Preferably used tertiary amines are triethanolamine, methyldiethanolamine, dimethylaminodiglycol, dimethylethanolamine and N,N,N',N'-tetra(hydroxyethyl)ethylenediamine. A further embodiment of the process according to the invention is described hereinafter.

The polymerizable aqueous mixture may, where appropriate, contain group (b) monomers. By these are meant other monoethylenically unsaturated monomers which are copolymerizable with monomers (a) and (c). These include, for example, the amides and nitriles of monoethylenically unsaturated carboxylic acids, e.g. acrylamide, methacrylamide and N-vinylformamide, acrylonitrile and methacrylonitrile, dialkyldiallylammonium halides such as dimethyldiallylammonium chloride, diethyldiallylammonium chloride, allylpiperidinium bromide, N-vinylimidazoles such as N-vinylimidazole, 1-vinyl-2-methylimidazole and N-vinylimidazolines such as N-vinylimidazoline, 1-vinyl-2-methylimidazoline, 1-vinyl-2-ethylimidazoline or 1-vinyl-2-propylimidazoline, which can be used in the form of the free bases, in quaternized form or as salt in the polymerization. Also suitable are dialkylaminoalkyl acrylates and dialkylaminoalkyl methacrylates, e.g. dimethylaminoethyl acrylate, dimethylaminoethyl methacrylate, diethylaminoethyl acrylate and diethylaminoethyl methacrylate. The basic esters are preferably used in quaternized form or as salt. Other suitable compounds of group (b) are, for example, vinyl esters of saturated $C_1$–$C_4$-carboxylic acids such as vinyl formate, vinyl acetate or vinyl propionate, alkyl vinyl ethers with at least 2 carbon atoms in the alkyl group, such as ethyl vinyl ether or butyl vinyl ether, esters of monoethylenically unsaturated $C_3$–$C_6$-carboxylic acids, e.g. esters of monohydric $C_1$–$C_{18}$-alcohols and acrylic acid, methacrylic acid or maleic acid, monoesters of maleic acid, e.g. monomethyl maleate, and hydroxyalkyl esters of said monoethylenically unsaturated carboxylic acids, e.g. 2-hydroxyethyl acrylate, hydroxypropyl acrylate, hydroxybutyl acrylate, hydroxyethyl methacrylate, hydroxypropyl methacrylate and hydroxybutyl methacrylate, N-vinyllactams such as N-vinyl-pyrrolidone or N-vinylcaprolactam, acrylic and methacrylic esters of alkoxylated monohydric saturated alcohols, e.g. of alcohols with 10 to 25 carbon atoms which have been reacted with 2 to 200 mol of ethylene oxide and/or propylene oxide per mol of alcohol, and monoacrylates and monomethacrylates of polyethylene glycol or polypropylene glycol, where the molecular weights ($M_N$) of the polyalkylene glycols can be, for example, up to 2000. Other suitable group (b) monomers are alkyl-substituted styrenes such as ethylstyrene or tert-butylstyrene. The group (b) monomers can also be used in a mixture with the other monomers, e.g. mixtures of vinyl acetate and 2-hydroxyethyl acrylate in any desired ratio, in the copolymerization.

The group (c) monomers have at least 2 ethylenic double bonds. Examples of monomers of this type, which are normally used as crosslinkers in polymerization reactions, are N,N'-methylenebisacrylamide, polyethylene glycol diacrylates and polyethylene glycol dimethacrylates which are derived in each case from polyethylene glycols with a molecular weight of from 106 to 8500, preferably 400 to 2000, trimethylolpropane triacrylate, trimethylolpropane trimethacrylate, ethylene glycol diacrylate, propylene glycol diacrylate, butanediol diacrylate, hexanediol diacrylate, hexanediol dimethacrylate, diacrylates and dimethacrylates of block copolymers of ethylene oxide and propylene oxide, polyhydric alcohols such as glycerol or pentaerythritol which are esterified two or three times with acrylic acid or methacrylic acid, triallylamine, tetraallylethylenediamine, divinylbenzene, diallyl phthalate, polyethylene glycol divinyl ethers of polyethylene glycols with a molecular weight of from 126 to 4000, trimethylolpropane diallyl ether, butanediol divinyl ether, pentaerythritol triallyl ether and/or divinylethyleneurea. Water-soluble crosslinkers are preferably used, e.g. N,N'-methylenebisacrylamide, polyethylene glycol diacrylates and polyethylene glycol dimethacrylates derived from adducts of 2 to 400 mol of ethylene oxide and 1 mol of a diol or polyol, vinyl ethers of adducts of 2 to 400 mol of ethylene oxide and 1 mol of a diol or polyol, ethylene glycol diacrylate, ethylene glycol dimethacrylate or triacrylates and trimethacrylates of adducts of 6 to 20 mol of ethylene oxide and one mol of glycerol, pentaerythritol triallyl ether and/or divinylurea.

Also suitable as crosslinkers are compounds which contain at least one polymerizable ethylenically unsaturated group and at least one other functional group. The functional group in these crosslinkers must be able to react with the functional groups, essentially the carboxyl groups or sulfo groups, in the monomers (a). Examples of suitable functional groups are hydroxyl, amino, epoxy and aziridino groups.

Also suitable as crosslinkers are those compounds which have at least two functional groups able to react with carboxyl and sulfo groups in the group (a) monomers used. The suitable functional groups have already been mentioned above, ie. hydroxyl, amino, epoxy, isocyanate, ester, amide and aziridino groups. Examples of such crosslinkers are ethylene glycol, diethylene glycol, triethylene glycol, tetraethylene glycol, polyethylene glycol, glycerol, polyglycerol, propylene glycol, polypropylene glycol, block copolymers of ethylene oxide and propylene oxide, sorbitan fatty acid esters, ethoxylated sorbitan fatty acid esters, trimethylolpropane, pentaerythritol, polyvinyl alcohol, sorbitol, polyglycidyl ethers such as ethylene glycol diglycidyl ether, polyethylene glycol diglycidyl ether, glycerol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and polypropylene glycol diglycidyl ether, polyaziridine compounds such as 2,2-bishydroxymethylbutanol tris[3-(1-aziridinyl)propionate], 1,6-hexamethylenediethyleneurea, 4,4'-methylenebis(phenyl)-N,N'-diethyleneurea, halo epoxy compounds such as epichlorohydrin and a-methylfluorohydrin, polyisocyanates such as 2,4-tolylene diisocyanate and hexamethylene diisocyanate, alkylene carbonates such as 1,3-di-oxolan-2-one and 4-methyl-1,3-dioxolan-2-one, polyquaternary amines such as condensates of dimethylamine with epichlorohydrin, homo- and copolymers of diallyldimethylammonium chloride, and homo- and copolymers of dimethylaminoethyl (meth)acrylate, which are, where appropriate, quaternized with, for example, methyl chloride.

Other suitable crosslinkers are polyvalent metal ions able to form ionic crosslinks. Examples of such crosslinkers are magnesium, calcium, barium and aluminum ions. A preferred crosslinker of this type is sodium aluminate. These crosslinkers are added, for example, as hydroxides, carbonates or bicarbonates to the aqueous polymerizable solution.

Other suitable crosslinkers are multifunctional bases which are likewise able to form ionic crosslinks, for example polyamines or their quaternized salts. Examples of polyamines are ethylenediamine, diethylenetriamine, triethylenetetramine, tetraethylenepentamine, pentaethylenehexamine and polyethyleneimines, and polyvinylamines with molecular weights of up to 4,000,000 in each case.

In a preferred embodiment of the invention, two different crosslinkers are used, one of which is soluble in water and the other is insoluble in water. The hydrophilic crosslinker which is soluble in the aqueous phase of the reaction mixture produces, in a conventional way, a relatively uniform crosslinking of the resulting polymer, as is conventional in the production of a superabsorbent. The hydrophobic crosslinker which is insoluble or has only limited solubility in the polymerizable aqueous mixture concentrates in the surfactant interlayer between the gas phase and the polymerizable aqueous phase. This means that, in the subsequent polymerization, the surface of the foam is more extensively crosslinked than is the interior of the superabsorbent hydrogel. This results in a core/shell structure of the foam directly in the production of the superabsorbent foam. Such extensive surface crosslinking of a superabsorbent foam is possible in the prior art production processes only by subsequent surface crosslinking of an expanded superabsorbent which has already been formed. In the conventional procedure, a separate process step is necessary for this subsequent crosslinking, but this can be omitted in the process of the present invention.

Products with a core/shell structure show distinctly improved properties compared with homogeneously crosslinked samples in respect of the absorption speed, distributing effect and gel stability. Apart from polyvalent metal ions, all the water-insoluble crosslinkers which are described above and can be assigned to the various groups are suitable for producing foams with a core/shell structure, ie. foams in which the entire surface is more highly crosslinked than the layer underneath, which has been referred to above as the core layer. Particulary preferred hydrophobic crosslinkers are diacrylates or dimethacrylates or divinyl ethers of alkanediols with 2 to 25 carbon atoms (branched, linear, with any suitable arrangement of OH groups) such as 1,3-propanediol, 1,4-butanediol, 1,6-hexanediol, neopentyl glycol, 1,9-nonanediol or 1,2-dodecanediol, di-, tri- or polypropylene glycol diacrylates or dimethacrylates, allyl acrylate, allyl methacrylate, divinylbenzene, glycidyl acrylate or glycidyl methacrylate, allyl glycidyl ether and bisglycidyl ethers of the alkanediols listed above.

Examples of suitable hydrophilic crosslinkers are N,N'-methylenebisacrylamide, polyethylene glycol diacrylates or dimethacrylates with a molecular weight MN of from 200 to 4000, divinylurea, triallylamine, diacrylates or dimethacrylates of adducts of from 2 to 400 mol of ethylene oxide and 1 mol of a diol or polyol or the triacrylate of an adduct of 20 mol of ethylene oxide and 1 mol of glycerol and vinyl ethers of adducts of from 2 to 400 mol of ethylene oxide and 1 mol of a diol or polyol.

The group (a) monomers are present in the polymerizable aqueous mixture in amounts of, for example, from 10 to 90, and preferably 20 to 85, % by weight. The group (b) monomers are used only where appropriate for modifying the superabsorbent foams and can be present in amounts of up to 50, preferably in amounts of up to 20, % by weight in the polymerizable aqueous mixture. The crosslinkers (c) are present in the reaction mixture in amounts of, for example, from 0.001 to 8, and preferably from 0.01 to 5, % by weight.

The polymerization initiators which can be used are all initiators which form free radicals under the polymerization conditions and which are normally used in the preparation of superabsorbents. It is also possible to initiate the polymerization by the action of electron beams on the polymerizable aqueous mixture. However, the polymerization can also be started in the absence of initiators of the abovementioned type by the action of high-energy radiation in the presence of photoinitiators.

Polymerization initiators which can be used are all compounds which decompose to free radicals under the polymerization conditions, eg. peroxides, hydroperoxides, hydrogen peroxide, persulfates, azo compounds and the redox catalysts. Water-soluble initiators are preferably used. It is advantageous in some cases to use mixtures of various polymerization initiators, e.g. mixtures of hydrogen peroxide and sodium or potassium peroxydisulfate. Mixtures of hydrogen peroxide and sodium peroxydisulfate can be used in any desired ratio. Examples of suitable organic peroxides are acetylacetone peroxide, methyl ethyl ketone peroxide, tertbutyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-trimethylhexanoate, acetyl cyclohexylsulfonyl peroxide, dilauroyl peroxide, dibenzoyl peroxide and tert-amyl perneodecanoate. Particularly suitable polymerization initiators are water-soluble azo initiators, eg. 2,2'-azobis(2-amidinopropane) dihydrochloride, 2,2'-azobis(N,N'-dimethyleneisobutyramidine) dihydrochloride, 2-(carbamoylazo)isobutyronitrile, 2,2'-azobis[2-(2-imidazolin-2-yl)propane] dihydrochloride and 4,4,-azobis (4-cyanovaleric acid). Said polymerization initiators are used in conventional amounts, e.g. in amounts of from 0.01 to 5, preferably 0.1 to 2.0, % of the weight of the monomers to be polymerized.

Also suitable as initiators are redox catalysts. The redox catalysts contain as oxidizing component at least one of the abovementioned peroxy compounds and as reducing component, for example, ascorbic acid, glucose, sorbose, ammonium or alkali metal bisulfite, sulfite, thiosulfate, hyposulfite, pyrosulfite or sulfide, metal salts such as iron(II) ions or silver ions, or sodium hydroxymethylsulfoxylate. The reducing component preferably used in the redox catalyst is ascorbic acid or sodium sulfite. Based on the amount of monomers used in the polymerization, for example, from $3 \times 10^{-6}$ to 1 mol % of the reducing component of the redox catalyst system and from 0.001 to 5.0 mol % of the oxidizing component of the redox catalyst are used.

If the polymerization is initiated by the action of high-energy radiation, photoinitiators are normally used as initiator. These may be, for example, α-splitters, H-abstracting systems or else azides. Examples of initiators of these types are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds like the free-radical formers mentioned above, substituted hexaarylbisimidazoles or acylphosphine oxides. Examples of azides are: 2-(N,N-dimethylamino) ethyl 4-azidocinnamate, 2-(N,N-dimethylamino)ethyl-4-azidonaphthyl ketone, 2-(N,N-dimethylamino)ethyl 4-azidobenzoate, 5-azido-1-naphthyl 2-(N,N-dimethylamino)ethyl sulfone, N-(4-sulfonylazidophenyl) maleimide, N-acetyl-4-sulfonylazidoaniline, 4-sulfonylazido-aniline, 4-azidoaniline, 4-azidophenacyl bromide, p-azidobenzoic acid, 2,6-bis(p-azidobenzylidene) cyclohexanone and 2,6-bis(p-azidobenzylidene)-4-methylcyclohexanone. The photoinitiators are, if employed, normally used in amounts of from 0.01 to 5% of the weight of the monomers to be polymerized.

The polymerizable aqueous mixtures contain as component (e) from 0.1 to 20% by weight of at least one surfactant. The surfactants are of crucial importance for the production and stabilization of the foam. Anionic, cationic or nonionic surfactants or mixtures of surfactants which are compatible with one another can be used. It is possible to employ low molecular weight or else polymeric surfactants, and combinations of different or else similar types of surfactants have proved to be advantageous. Examples of non-ionic surfactants are adducts of alkylene oxides, in particular ethylene oxide, propylene oxide and/or butylene oxide, and alcohols, amines, phenols, naphthols or carboxylic acids. Surfactants advantageously used are adducts of ethylene oxide and/or propylene oxide and alcohols containing at least 10 carbon atoms, where the adducts contain from 3 to 200 mol of ethylene oxide and/or propylene oxide per mol of alcohol. The adducts contain the alkylene oxide units in the form of blocks or in random distribution. Examples of nonionic surfactants are the adducts of 7 mol of ethylene oxide and 1 mol of tallow fatty alcohol, products of the reaction of 9 mol of ethylene oxide with 1 mol of tallow fatty alcohol and adducts of 80 mol of ethylene oxide and 1 mol of tallow fatty alcohol. Other commercial nonionic surfactants consist of products of the reaction of oxo alcohols or Ziegler alcohols with 5 to 12 mol of ethylene oxide per mol of alcohol, in particular with 7 mol of ethylene oxide. Other commercial nonionic surfactants are obtained by ethoxylation of castor oil. For example, from 12 to 80 mol of ethylene oxide are added on per mol of castor oil. Further commercial products are, for example, the products of the reaction of 18 mol of ethylene oxide with 1 mol of tallow fatty alcohol, the adducts of 10 mol of ethylene oxide and 1 mol of a $C_{13}/C_{15}$ oxo alcohol, or the products of the reaction of 7 to 8 mol of ethylene oxide and 1 mol of a $C_{13}/C_{15}$ oxo alcohol. Other suitable nonionic surfactants are phenol alkoxylates such as p-tert-butylphenol which has been reacted with 9 mol of ethylene oxide, or methyl ethers of products of the reaction of 1 mol of a $C_{12}$–$C_{18}$-alcohol and 7.5 mol of ethylene oxide.

The nonionic surfactants described above can be converted, for example, by esterification with sulfuric acid into the corresponding sulfuric acid half esters. The sulfuric acid half esters are employed as anionic surfactants in the form of the alkali metal or ammonium salts. Examples of suitable anionic surfactants are alkali metal or ammonium salts of sulfuric acid half esters of adducts of ethylene oxide and/or propylene oxide and fatty alcohols, alkali metal or ammonium salts of alkylbenzene-sulfonic acid or of alkylphenol ether sulfates. Products of said type are commercially available. Examples of commercial anionic surfactants are the sodium salt of a sulfuric acid half ester of a $C_{13}/C_{15}$ oxo alcohol which has been reacted with 106 mol of ethylene oxide, the triethanolamine salt of dodecylbenzene-sulfonic acid, the sodium salt of alkylphenol ether sulfates and the sodium salt of the sulfuric acid half ester of a product of the reaction of 106 mol of ethylene oxide with 1 mol of tallow fatty alcohol. Other suitable anionic surfactants are sulfuric acid half esters of $C_{13}/C_{15}$ oxo alcohols, paraffin-sulfonic acids such as $C_{15}$-alkylsulfonate, alkyl-substituted benzenesulfonic acids and alkyl-substituted naphthalene-sulfonic acids such as dodecylbenzenesulfonic acid and di-n-butylnaphthalenesulfonic acid, and fatty alcohol phosphates such as $C_{15}/C_{18}$ fatty alcohol phosphate. The polymerizable aqueous mixture may contain combinations of a nonionic surfactant and an anionic surfactant or combinations of nonionic surfactants or combinations of anionic surfactants. Cationic surfactants are also suitable. Examples thereof are the products, quaternized with dimethyl sulfate, of the reaction of 6.5 mol of ethylene oxide with 1 mol of oleylamine, distearyldimethylammonium chloride, lauryltrimethylammonium chloride, cetylpyridinium bromide and the triethanolamine ester of stearic acid which is quaternized with dimethyl sulfate and is preferably used as cationic surfactant.

The surfactant content of the polymerizable aqueous mixture is 0.1 to 20, preferably 0.5 to 10, % by weight. In most cases, the polymerizable aqueous mixtures have a surfactant content of from 1.5 to 6% by weight.

The polymerizable aqueous mixtures may contain as component (f), where appropriate, at least one solubilizer. By this are meant water-miscible organic solvents, e.g. alcohols, glycols, polyethylene glycols and monoethers derived therefrom, the monoethers containing no double bonds in the molecule. Suitable ethers are methylglycol, butylglycol, butyldiglcyol, methyldiglycol, butyltriglycol, 3-ethoxy-1-propanol and glycerol monomethyl ether.

The polymerizable aqueous mixtures contain 0 to 50% by weight of at least one solubilizer. If solubilizers are used, their content in the polymerizable aqueous mixture is preferably up to 25% by weight.

The polymerizable aqueous mixture may, where appropriate, contain thickeners, foam stabilizers, polymerization regulators, fillers and cell nucleating agents. Thickeners are used, for example, to optimize the foam structure and to improve the foam stability. This results in only slight shrinkage of the foam during the polymerization. Suitable thickeners are all natural and synthetic polymers which are known for this purpose and which greatly increase the viscosity of an aqueous system. These may be water-swellable or water-soluble synthetic and natural polymers. Superabsorbents in powder form are also suitable as thickeners. A detailed review of thickeners is to be found, for example, in the publications by R. Y. Lochhead and W. R. Fron, Cosmetics & Toiletries, 108, 95–135 (May 1993) and M. T. Clarke, "Rheological Additives" in D. Laba (Ed.) "Rheological Properties of Cosmetics and Toiletries", Cosmetic Science and Technology Series, Vol. 13, Marcel Dekker Inc., New York 1993.

Water-swellable or water-soluble synthetic polymers suitable as thickeners are, for example, high molecular weight polymers of the monoethylenically unsaturated monomers which contain acidic groups described above under (a). Examples.of thickeners of this type are high molecular weight homopolymers of acrylic acid and/or methacrylic acid or slightly crosslinked copolymers of acrylic acid and/or methacrylic acid and a compound which contains at least 2 ethylenic double bonds, e.g. butanediol diacrylate. Also suitable are high molecular weight polymers of acrylamide and methacrylamide or copolymers of acrylic acid and acrylamide with molecular weights of more than 1 million. Copolymers of this type are known as thickeners. Other known thickeners are high molecular weight polyethylene glycols or copolymers of ethylene glycol and propylene glycol, and high molecular weight polysaccharides such as starch, gum guar, locust bean gum or derivatives of natural substances such as carboxymethylcellulose, hydroxyethylcellulose, hydroxymethylcellulose, hydroxypropylcellulose and cellulose mixed ethers. Another group of thickeners comprises water-insoluble products such as finely divided silicon dioxide, pyrogenic silicas, precipitated silicas in hydrophilic or hydrophobic modifications, zeolites, titanium dioxide, cellulose powder, or other fine-particle powders of crosslinked polymers which are different from superabsorbents. The polymerizable aqueous mixtures may contain the thickeners in amounts of up to 30% by weight. If such thickeners are in fact used, they are present in the polymerizable aqueous mixture in amounts of from 0.1, preferably 0.5, to 20% by weight.

In order to optimize the foam structure, it is possible where appropriate to add hydrocarbons with at least 5 carbon atoms in the molecule to the aqueous reaction mixture. Examples of suitable hydrocarbons are pentane, hexane, cyclohexane, heptane, octane, isooctane, decane and dodecane. The suitable aliphatic hydrocarbons may be straight-chain, branched or cyclic and have a boiling point which is above the temperature of the aqueous mixture during the foaming. The aliphatic hydrocarbons increase the pot life of the foamed aqueous reaction mixture which has not yet polymerized. This facilitates the handling of the foams which have not yet polymerized and increases the reliability of the process. The hydrocarbons are used in amounts of from 0 to 10% of the weight of the polymerizable aqueous mixture. When they are used, the amounts preferably present in the aqueous mixture are from 0.1 to 5% by weight.

In order to alter the properties of the superabsorbents, for example the absorption speed and the absorption capacity for water, it may be advantageous to add a polymerization regulator or a mixture of several polymerization regulators to the aqueous reaction mixture. Examples of suitable polymerization regulators are formic acid, thio compounds such as 2-mercaptoethanol, mercaptopropanol, mercaptobutanol, dodecyl mercaptan, thioglycolic acid or amines such as triethylamine, morpholine or piperidine. The amounts of polymerization regulators can be up to 10% of the weight of the monomers used. If polymerization regulators are used, preferably from 0.1 to 5% of the weight of the monomers is used.

The constituents indicated under (g) which are to be used optionally, can be employed singly or in a mixture in the production of the polymers according to the invention. However, the absence of thickeners, foam stabilizers, fillers, cell nucleating agents and polymerization regulators is also possible.

In the production, according to the invention, of water-absorbing, expanded, crosslinked polymers the first stage of the process is foaming of the polymerizable aqueous mixture described above. For this purpose, a gas which is inert to free radicals is dispersed in the form of fine bubbles in the aqueous monomer phase in such a way that a foam is formed. Gas bubbles are introduced into a monomer mixture, for example, using beating, shaking, stirring or whipping devices. It is furthermore possible to produce such foams by gases flowing out of a liquid-covered orifice or by utilizing turbulence manifestations in flows. Finally, it is also possible to use the formation of lamellae on wires or screens for this purpose. These various methods may also be combined with one another where appropriate. Examples of suitable gases which are inert to free radicals are nitrogen, carbon dioxide, helium, neon and argon. Nitrogen is preferably used.

The foam is produced according to the invention separately from the polymerization. The polymerizable aqueous mixture can be foamed, for example, in industrial apparatus known for producing urea/formaldehyde foams, cf. Frisch and Saunders, Polymeric Foams Part II, page 679 et seq. (1973). Foaming of the polymerizable aqueous mixture in the laboratory can most simply take place in a conventional kitchen appliance equipped with whisks. Mechanical generation of foam is preferably carried out in an inert gas atmosphere. Examples of inert gases which can be used are nitrogen, the inert gases and carbon dioxide. The foam is produced by combining all the components of the reaction mixture. The procedure for this is expediently first to dissolve all the water-soluble components in water and only then to add the water-insoluble substances. It may also be advantageous, depending on the process used for mechanical generation of the foam and depending on the initiator present in the polymerizable aqueous mixture, to add the initiator only at the end of the foaming process. The consistency of the mechanically produced foams can be varied in a wide range. Thus, it is possible to produce either foams which flow readily or else rigid foams which can be cut. It is likewise possible to vary the average size of the gas bubbles, their size distribution and their arrangement in the liquid matrix by the selection of the surfactants, the solubilizers, thickeners and foam stabilizers, cell nucleating agents, the temperature and the foaming technique within a wide range so that it is possible in a simple way to adjust the density, open-cell character or wall thickness of the matrix material. The temperatures of the polymerizable aqueous mixture during the foaming process are in the range from −10 to 100, preferably 0 to +50° C. The temperatures used during the production of the foam are in every case below the boiling point of constituents of the polymerizable aqueous mixture. The foam can also be produced under elevated pressure, e.g. 1.5 to 25 bar, but atmospheric pressure is preferred.

An essential advantage of the production, according to the invention, of expanded superabsorbents compared with processes hitherto disclosed for producing such foams is to be regarded as being the obtaining, in the first stage of the process according to the invention, of foamed, polymerizable aqueous mixtures which are stable over a lengthy period, e.g. up to 6 hours, so that they can be handled without problems, for example. The expanded mixtures which have not yet polymerized can, for example, be placed in a suitable mold for the subsequent polymerization in order to produce molded articles required for a particular application. Waste foam which is possibly produced on shaping the foamed polymerizable aqueous mixture can be returned directly to the process. The foamed polymerizable material can, for example, be applied in the required thickness to a temporary substrate, which is advantageously provided with a non-stick coating. It is possible, for example, to apply the foam to a substrate with a knife. Another possibility is to introduce the polymerizable expanded aqueous mixture into molds which likewise have a non-stick coating, and to polymerize the foam completely therein.

Since the foamed polymerizable aqueous mixture has a long pot life, this mixture is also suitable for producing composite materials. Thus, for example, the polymerizable foam produced mechanically can be applied to a permanent substrate, e.g. sheets composed of polymers (eg. polyethylene, polypropylene or polyamide sheets) or metals, nonwovens, fluff, tissues, woven fabric, natural or synthetic fibers, or to other foams. In the production of composite materials it may in some circumstances also be advantageous to apply the polymerizable foam in the form of particular structures or in layers differing in thickness to a substrate. However, it is also possible to apply the polymerizable foam to fluff layers and to impregnate them in such a way that the fluff is, after the polymerization, an integral constituent of the foam. The foamed polymerizable aqueous mixture obtainable in the first stage of the process can also be shaped to large blocks and polymerized. The blocks can, after the polymerization, be cut or sawn to smaller shaped articles. It is also possible to produce sandwich-like structures by applying a foamed polymerizable aqueous mixture to a substrate, to cover the expanded layer with a sheet, nonwovens, tissues, woven fabrics, fibers or other foams, where appropriate of a material differing from the one used first, and again to apply foam and, where appropriate, to cover with another sheet, nonwovens, tissues, woven fabrics, fibers or other foams. The composite is then subjected to the polymerization in the second stage of the process. However, sandwich-like structures with other foam layers can also be produced.

In the second stage of the process for producing the superabsorbing foams according to the invention, the foamed polymerizable aqueous mixture is polymerized. The polymerization can take place, depending on the initiator used, by increasing the temperature, by exposure to light, by exposure to electron beams or else by increasing the temperature and exposing to light. The temperature of the foamed polymerizable aqueous mixture can be increased by using all processes customary in industry, for example bringing the foam into contact with heatable plates, exposure of the polymerizable foam to infrared radiation, or heating with microwaves. Foam layers according to the invention with a layer thickness of up to about 1 millimeter are produced, for example, by heating on one side or, in particular, by irradiating on one side. If relatively thick layers of a foam are to be produced, eg. foams with thicknesses of several centimeters, heating of the polymerizable foamed material by a microwave is particularly advantageous because relatively uniform heating can be achieved in this way. The polymerization is in this case carried out, for example, at temperatures from 20 to 180, preferably in the range from 20 to 100, ° C.

Foam layers of intermediate thicknesses, i.e. with a thickness in the range from about 1 millimeter to about 2 centimeters, such as from about 2 millimeters to about 1 centimeter, are preferably produced in the following way: instead of initiating the polymerization on only one surface, initiation is brought about on both surfaces by exposing a layer of the composition foamed according to the invention to heat treatment and/or irradiation with light on both surfaces. Treatment of both surfaces of the foam layer can take place according to the invention synchronously or asynchronously in any time sequence or in a deferred fashion. It is possible, for example, for the heat treatment of both surfaces of a foam layer to be carried out simultaneously or in a deferred fashion on one occasion or several occasions per surface. The procedure on irradiation with light can be likewise. However, it is also possible to treat each surface both with heat and with light, and exposure to heat and light can take place simultaneously or in any sequence, on one occasion or several times on the same surface of the foam layer. However, it is usually most expedient to use heat and/or light once on each surface of the foam layer.

Since the heat treatment expediently takes place by contact heating, and the support material used for this purpose usually does not transmit light, polymerization initiation on both sides is most expediently carried out by contact heating one surface and, for example simultaneously, irradiating the opposite surface. This variant of the process, and the contact heating on both sides, are particularly suitable for producing composite materials.

The heat treatment usually takes place in the case of polymerisation initiation on both surfaces in a range from about 50 to about 200° C., preferably at about 80 to about 1600° C. Typical contact times are in this case about 0.5 to about 25 minutes for each surface of the film layer, preferably about 2 to about 15 minutes. The light used for the irradiation is preferably from the UV/VIS region, i.e. light from the ultraviolet or visible region of the spectrum, such as, for example, light with a wavelength in the range from about greater than 200 nm up to about 750 nm, for example about 250 nm to about 700 nm, such as, for example, UV-A radiation of wavelength 315 to 400 nm. The duration of the irradiation can likewise be in the range from about 0.1 to about 25 minutes, preferably about 0.5 to 10 minutes, for each surface of the foam layer.

On combined heat treatment and irradiation of the same or opposite surfaces of the foam layer, the respective duration of heat treatment and irradiation can be identical or different. Depending on the composition and thickness of the foam layer, nature and quantity of the polymerization initiators used, intensity and wavelength of the light, and temperature of the contact heating device and other criteria, however, it may be advantageous to carry out the heat treatment and irradiation over time intervals of different lengths. The chosen time intervals may, for example, follow one another in time. For example, heating of the first surface for, for example, 3 minutes can be followed by irradiation of the opposite second surface for, for example, 2 minutes. This can be followed where appropriate by a heat treatment of the first and/or the second surface for, for example, 2 minutes. This treatment rhythm can, where appropriate, be repeated one or more times with retention or alteration of the chosen time intervals. The chosen time intervals may, however, also overlap. For example, in this case the irradiation can be maintained for only part of the heat-treatment interval. Thus, for example, the first surface of the foam layer can be heated, for example, for 2 minutes and then heated, for example, for a further 4 minutes and, synchronously with this, the opposite surface can be irradiated for 4 minutes. It is likewise conceivable initially to heat or to irradiate the two surfaces synchronously for, for example, 3 minutes and then to continue the heat treatment of one surface, for example for 2 minutes, after the irradiation of the other surface has been completed. These treatment rhythms can also be repeated one or more times where appropriate with retention or alteration of the chosen time intervals.

When the polymerization is initiated by exposing the foamed polymerizable material to light it is possible to use all conventional light-exposure systems as long as their emission spectrum is suited to the photoinitiator used. When the polymerization is initiated by exposure to light it is advantageous to use a combination of a photoinitiator and a thermal initiator and/or a photoinitiator which can also act as thermal initiator, e.g. azo initiators. Since the foam becomes very hot during the polymerization due to the high heat of polymerization, the polymerization reaction takes place particularly fast and efficiently in this way. On initiation by exposure to light, the polymerization temperature is in the range from 0 to 150, preferably 10 to 100°C.

A considerable advantage of the process according to the invention is to be regarded as the fact that the polymerization takes place with substantial retention of the structure of the foamed polymerizable aqueous mixture, ie. the volume of the polymerizable foam changes negligibly during the polymerization. The polymerization reaction is influenced by the temperature at the start, the initiation technique or the removal of heat. The polymerization temperature is preferably controlled so that boiling of the polymerizable aqueous mixture is avoided. As the polymerization advances, the foam solidifies as a consequence of increasing gel formation. The foam has at least partially an open-cell structure. It is preferably more than 75% open-celled.

The foams resulting after the polymerization have a water content between 10% and 80%. It is possible in principle by using alkanolamines to obtain foams which are flexible even in the dried state. However, since the foams are hygroscopic and anyway absorb moisture from the air, it is sensible to leave a residual moisture content in the region of 1–20, preferably 5–15, % by weight in the foam. It may also be worthwhile, depending on the composition of the foam and the intended area of use, to adjust the moisture content in the foam to differ from this.

The foam can be dried by conventional techniques, for example by heating with a stream of hot gas, by reducing the pressure, by exposure to infrared radiation or by heating with microwaves. Microwaves once again prove to be advantageous in this case for drying large-volume shaped articles. The temperature during the drying should be less than 180° C., preferably less than 120° C. It may be advantageous to dry with a stream of gas having a defined moisture content (up to the use of steam) so that the foam is dried only to a defined moisture content in this way.

The process according to the invention results in a superabsorbent foam which is predominantly open-celled, preferably at least 75% open-celled.

As indicated above, an inhomogeneous crosslink density can be produced even during the production of the superabsorbent foams according to the invention. This is particularly advantageous when the monomers used as the components, described above, are (a) acrylic acid, methacrylic acid, vinylsulfonic acid, acrylamidopropanesulfonic acid or mixtures thereof, and (c) a mixture of at least one water-soluble and at least one water-insoluble crosslinker.

It may, nevertheless, be desirable subsequently to alter the degree of crosslinking of the foam. In order to achieve this, for example, it is possible to incorporate latent crosslinkage points in the gel during the polymerization by adding suitable monomers, these points not leading to crosslinking reactions under the conditions of production of the foam but being able under specific conditions which can be applied subsequently, e.g. by greatly increasing the temperature, to form further crosslinkage points in the gel structure. Examples which can serve for such monomers are hydroxyl-containing compounds which are able at elevated temperature, ie. above 150° C., to react with the carboxyl groups in the foam structure. Examples of compounds suitable as latent crosslinkage points are hydroxyethyl acrylate, hydroxypropyl acrylate, hydroxybutyl acrylate, monoacrylic esters of glycerol, monoacrylates or monometh-acrylates of polyethylene glycols with at least 2 ethylene glycol units, monoacrylates or monomethacrylates of polypropylene glycols with at least 2 propylene glycol units and monomethacrylates of polyhydric alcohols, e.g. hydroxybutyl methacrylate, hydroxypropyl methacrylate, hydroxyethyl methacrylate or glycerol monomethacrylate.

Another possibility for homogeneous subsequent crosslinking is provided by subsequent addition of crosslinking reagents, ie. compounds which have at least two reactive groups which are able, under suitable conditions, e.g. on heating to at least 70° C., to react with the acidic groups in the expanded hydrogel. In this case it is also possible to achieve, controlled by the depth of penetration of the crosslinker, a modification of the inhomogeneous crosslink density. Suitable crosslinkers form covalent or ionic bonds with the carboxyl groups of the polymer matrix. Suitable crosslinkers are compounds which have at least two functional groups of the same or different types, e.g. hydroxyl, amino, quaternary ammonium, isocyanato, epoxy, aziridino, ester or amide groups. Preferred subsequent crosslinkers are polyalcohols such as glycerol, butylene glycol, propylene glycol or bisepoxides. With such crosslinkers it is possible for the reaction to be carried out, for example, in the temperature range of 70–170, preferably 100–160° C. The application of the crosslinkers to the foamed material can take place, for example, by spraying, dipping or gas-deposition.

It is possible according to the invention, however, to produce a foam with a lower degree of neutralization, typically between 0 and 60%, preferably 15 to 40%, and definitively intended and to apply at least one alkanolamine subsequently, for example by spraying on the alkanolamines or solutions thereof in solvents or solvent mixtures. Examples of solvents which can be used for alkanolamines are: water, methanol, ethanol, isopropanol and acetone. Water is preferred. The subsequent neutralization expediently takes place after the polymerization and before the drying. However, it is also possible to apply at least one alkanolamine to the expanded hydrogel at a later time during the process.

This procedure is obligatory for use in secondary and primary alkanolamines. Tertiary alkanolamines can—as described above—be employed to neutralize the monomers (a) and, in addition, just like primary, secondary and quaternary alkanolamines, be used to neutralize the acidic groups in the expanded hydrogel after the polymerization. In some cases it has emerged that an advantageous procedure is for the monomers (a) containing acidic groups to be firstly partially neutralized with a tertiary alkanolamine (e.g. 20–50 mol %) and then polymerized, and subsequently for the remaining free acidic groups in the expanded hydrogel to be neutralized with an alkanolamine, preferably a primary alkanolamine such as ethanolamine, with the total degree of neutralization of the acidic groups in the hydrogel being 55 to 95, preferably 65 to 85, mol %.

The alkanolamines used can be primary, secondary, tertiary or quaternary and be monofunctional, difunctional or polyfunctional bases. The alkanolamines may in addition to their amino and hydroxyl groups have other functional groups such as ester, urethane, ether, thioether and urea groups. It is possible to employ, for example, low molecular weight compounds such as triethanolamine, methyldiethanolamine, dimethylethanolamine, ethanolamine, N-hydroxyethylmorpholine, dimethylaminodiglycol, N,N,N',N'-tetra(hydroxyethyl)ethylenediamine, N,N,N',N'-tetra(hydroxypropyl)ethylenediamine, dimethylaminotriglycol, diethylaminoethanol, 3-dimethylamino-1,2-propanediol, triisopropanolamine, diisopropylaminoethanol, choline hydroxide, choline carbonate, 2-tert-butylaminoethanol, tris(oxymethyl)aminomethane, 3-amino-1-propanol, isopropanolamine, 2-(2-aminoethoxy)ethanol, 2-amino-2-ethyl-1-propanol or else oligomers or polymers such as polymers or condensates with amino groups, such as polyethyleneimines or polyvinylamines, which have been reacted with ethylene oxide, propylene oxide, glycidol or other epoxides, or products of the reaction of at least bifunctional, low molecular weight alkanolamines with at least bifunctional reagents able to react either with the hydroxyl or with the amino group of the alkanolamines, such as carboxylic acids, esters, epoxides, isocyanates.

Suitable and preferred are triethanolamine, methyldiethanolamine, dimethylaminodiglycol, dimethylethanolamine, ethanolamine and/or N,N,N',N'-tetra(hydroxyethyl)ethylenediamine.

The resulting alkanolamine-containing foams are tacky. The tackiness can be completely eliminated by dusting with fine-particle powders. In principle, all organic or inorganic materials in the form of fine powders are suitable as long as they are hydrophilic, such as fine-particle silica (Aerosil®), silicates, talc, guar flour, tara flour, carob flour, all types of starches, crosslinked or uncrosslinked polyacrylic acids or salts thereof, polyvinyl alcohols, copolymers of maleic acid, titanium dioxide, zeolites, cellulose, carboxymethylcellulose and hydroxyethylcellulose. Water-insoluble materials are preferred, especially talc and Aerosil®. The dusting is expediently carried out after the polymerization, but may be carried out at any later time during the production process. The application rates are, for example, between 0.01 and 10%, preferably between 0.1 and 5%, based on the weight of the foam.

The superabsorbent foams according to the invention have a density of, for example, from $10^{-3}$ to 0.9, preferably 0.05 to 0.7, g/cm$^3$. The density of superabsorbent foams is determined by gravimetry. Squares with sides 5 cm long are cut, for example with a sharp knife, out of a uniform foam layer with a defined thickness of from 3 to 5 mm. These samples are weighed, and the resulting weight is divided by the volume calculated from the dimensions.

The absorption capacity of the expanded superabsorbent in water per gram of superabsorbent is determined on pieces of foam which have a thickness of 3 mm and each weigh 1 g. The retention is in this case tested by the teabag test. The liquid used in this case is a 0.9% strength sodium chloride solution. 1 g of the expanded material is packed into a teabag which is then closed. Care should be taken here to ensure that the teabag offers sufficient space for complete swelling. The teabag is then immersed in the liquid for a defined time and, after a drip time of 10 minutes, reweighed. To calculate the absorption capacity it is necessary to carry out a blank test in which a teabag without expanded superabsorbent is immersed in the solution, and the weight of the teabag is determined after the drip time of 10 minutes indicated above. The absorption capacity then results from the following equation (1):

$$\text{Absorption capacity} = \frac{\text{Weight of the teabag with superabsorbent foam} - \text{weight of the teabag in the blank test}}{\text{Weight of the superabsorbent foam}} \quad (1)$$

The absorption speed (referred to as AS hereinafter) was determined by cutting out, using a sharp knife, rectangular samples weighing 1 g from foam layers with a uniform thickness of 3 mm. These samples were placed in a Petri dish and 20 g of simulated urine were poured on. A stopclock was used to determine the time taken by the foam to absorb the simulated urine completely. The absorption speed (AS) in g/g·sec is calculated from the following equation (2):

$$AS = 20 \text{ g}/[1 \text{ g} \times \text{measured time (in sec)}] \quad (2)$$

Composition of Simulated Urine

The following salts are dissolved in 1 l of distilled water:
2.00 g KCl
2.00 g Na$_2$SO$_4$
0.85 g NH$_4$H$_2$PO$_4$
0.15 g (NH$_4$)$_2$HPO$_4$
0.19 g CaCl$_2$
0.23 g MgCl$_2$ The salts must be anhydrous.

Determination of the Monomer Foam Density

Exactly 100 ml of the monomer foam are introduced into a measuring cylinder, and the weight of this foam volume is determined. The density is obtained in g/cm$^3$ by dividing the rate found in g by 100.

Flexibility Determination

Defined humidities are adjusted in Plexiglass chambers, Bola standard desiccator V1854–01 supplied by Bohlender, at 20° C. by introducing into the chambers saturated solutions of specific salts which are in contact with an undissolved sediment. The following salts are used:

| | |
|---|---|
| 15% rel. humidity | LiCl monohydrate |
| 20% rel. humidity | potassium acetate |
| 32% rel. humidity | CaCl$_2$ hexahydrate |

Dried pieces of each foam about 2 cm×2 cm in size are introduced into these chambers, and the change in the moisture content in the foams is followed by gravimetry until the samples have reached the equilibrium state.

The Flexibility Is then Assessed on a Four-point Scale

| | |
|---|---|
| flexible | the sample can easily be bent through 180° and feels soft, |
| resilient | the sample can now be bent through 180° only with difficulty but does not break, |
| scarcely flexible | the sample can still be bent, but breaks between 90° and 180°, |
| rigid | the sample breaks even on bending by less than 90°. |

The flexibility is determined at elevated temperature using a conditioning cabinet supplied by Weiβ, type 125 SG+10JU/70DU, which allows the temperature and relative humidity to be specifically set.

To determine the flexibility at low temperatures, foam samples are moistened to a water content of 10% by spraying. This water content corresponds to the equilibrium water uptake at a relative humidity of 20%. The samples are then cooled in closed polyethylene bags to the appropriate temperature overnight, and their flexibility at the temperature set in each case is assessed according to the above criteria.

The water-absorbing, expanded, crosslinked polymers described above can be used for all purposes for which expanded superabsorbents described in the literature are employed. They are used, for example, in hygiene articles employed to absorb body fluids and in dressing material for covering wounds. They are suitable, for example, as water-absorbing constituent in diapers, sanitary towels and incontinence articles. They can be employed in the form of composite materials. Expanded superabsorbents can additionally be used as sealing material, as soil improver, as soil substitute and as packaging material. Specific embodiments of articles which contain expanded superabsorbents are described in detail, for example, in WO-A-94/22502. The expanded superabsorbents are additionally suitable for dewatering sludges, for thickening water-based surface coatings, e.g. for the disposal of residual amounts of unused water-based surface coatings or paints, by adding, for example, expanded superabsorbents in powder form to water-based surface coating residues until solidification occurs. The expanded, water-absorbing, crosslinked polymers can additionally be used for removing water from oils which contain water. They can be employed, for example, in the form of a powder with an average particle diameter of 150 μm to 5 mm in the applications described above.

The foams described above can, by reason of their properties, carry out various functions in hygiene articles in the storage of body fluids:
acquisition
distribution and/or
storage The foams perform the storage of body fluids entirely, whereas other constituents, such as high loft nonwovens, polypropylene nonwovens, polyester nonwovens or chemically modified celluloses, may be used to assist, as layer on the foams, the acquisition and distribution functions.

The percentage data in the examples are percent by weight unless otherwise evident from the context.

EXAMPLES

The flexibility and the absorption properties of the foams obtained in the examples and comparative examples are indicated in Tables 1–3.

Example 1

The following components were mixed in a tube closed with a screw cap using a magnetic stirrer:

| | |
|---|---|
| 105.39 g | of acrylic acid (1.46 mol) |
| 158.03 g | of a 37.3% strength sodium acrylate solution in water (0.63 mol) |
| 9.25 g | of guar flour |
| 1.85 g | of polyethylene glycol diacrylate of polyethylene glycol of molecular weight 500 |
| 58.58 g | of a 15% strength aqueous solution of an adduct of 80 mol of ethylene oxide and 1 mol of a linear saturated $C_{16}C_{18}$ fatty alcohol |
| 35.90 g | of water |

The resulting homogeneous mixture was introduced into a closed 2 l flask with cooling jacket and dropping funnel, into which carbon dioxide was passed from below. Two BOKU egg whisks connected via gears to an IKA RW28W stirrer were inserted into the flask. The carbon dioxide stream was adjusted so that it bubbled at a rate of 100 l/h through the reaction mixture. The stirrer motor was initially adjusted to a speed of 200 rpm, and carbon dioxide was passed through the mixture for 20 min to remove dissolved oxygen. During this time, 140.26 g of triethanolamine (0.94 mol) were added dropwise with cooling so that a final temperature of 16° C. was reached.

Subsequently, 4.63 g of pentane and 20.97 g of a 3% strength solution of 2,2'-azobis(2-amidinopropane) dihydrochloride in water were added, and the stirrer speed was increased to 735 rpm. The mixture was beaten at this speed for 3.5 min. After the end of the beating period, a fine-cell, free-flowing foam was obtained.

The resulting monomer foam was placed in a DIN A3-sized glass plate with edges 3 mm high and covered with a second glass plate. The foam sample was irradiated synchronously from both sides with two UV/VIS lamps (H öhnle UV 1000) for 4 minutes.

The resulting foam layer was dusted on both sides with about 0.3 g of talc and completely dried in a vacuum oven at 70° C. To determine the properties, part of the foam was subsequently adjusted to a moisture content of 10% by spraying with water.

Degree of neutralization: 75 mol %
Monomer foam density: 0.33 g/cm$^3$
Polymer foam density: 0.44 g/cm$^3$
Handle: dry, completely tack-free

Example 2

The following components were mixed in a tube closed with a screw cap using a magnetic stirrer:

| | |
|---|---|
| 52.68 g | of acrylic acid (0.73 mol) |
| 330.79 g | of a 40.0% strength triethanolammonium acrylate solution in water (0.60 mol) |
| 9.25 g | of guar flour |
| 1.85 g | of polyethylene glycol diacrylate of a polyethylene glycol of molecular weight 500 |
| 12.33 g | of a 15% strength aqueous solution of an adduct of 80 mol of ethylene oxide and 1 mol of a linear saturated $C_{16}C_{18}$ fatty alcohol |
| 102.34 g | of water |

The resulting homogeneous mixture was introduced into a closed 2 l flask with cooling jacket, into which carbon dioxide was passed from below. Two BOKU egg whisks connected via gears to an IKA RW28 W stirrer were inserted into the flask. The carbon dioxide stream was adjusted so that it bubbled at a rate of 100 l/h through the reaction mixture. The stirrer motor was initially adjusted to a speed of 200 rpm, and carbon dioxide was passed through the mixture for 20 min to remove dissolved oxygen. During this time, the internal temperature was cooled to 16° C. with the aid of the cooling jacket and a thermostat.

Subsequently, 4.63 g of pentane and 20.97 g of a 3% strength solution of 2,2'-azobis(2-amidinopropane) dihydrochloride in water were added, and the stirrer speed was increased to 735 rpm. The mixture was beaten at this speed for 3.5 min. After the end of the beating period, a fine-cell, free-flowing foam was obtained.

The resulting monomer foam was placed in a DIN A3-sized glass plate with edges 3 mm high and covered with a second glass plate. The foam sample was irradiated synchronously from both sides with two UV/VIS lamps (H öhnle UV 1000) for 4 minutes.

The resulting foam layer was dusted on both sides with about 0.3 g of talc and completely dried in a vacuum oven at 70° C. To determine the properties, part of the foam was subsequently adjusted to a moisture content of 10% by spraying with water.

Degree of neutralization: 45.0 mol %
Monomer foam density: 0.29 g/cm$^3$
Polymer foam density: 0.35 g/cm$^3$
Handle: dry, completely tack-free

Example 3

A foam was produced in the same manner as in Example 1 starting from the following starting materials:

| | |
|---|---|
| 127.96 g | of acrylic acid (1.78 mol) |
| 79.02 g | of a 37.3% strength sodium acrylate solution in water (0.31 mol) |
| 9.25 g | of guar flour |
| 1.85 g | of polyethylene glycol diacrylate of a polyethylene glycol of molecular weight 400 |
| 58.58 g | of a 15% strength aqueous solution of an adduct of 80 |

|         |                                                                                                                 |
|---------|-----------------------------------------------------------------------------------------------------------------|
|         | mol of ethylene oxide and 1 mol of a linear saturated $C_{16}C_{18}$ fatty alcohol |
| 45.58 g | of water |
| 187.01 g | of triethanolamine (1.25 mol) |
| 4.63 g | of pentane |
| 20.97 g | of a 3% strength solution of 2,2'-azobis(2-amidino-propane) dihydrochloride in water |

Degree of neutralization: 75 mol %
Monomer foam density: 0.34
Polymer foam density: 0.48
Handle: dry, completely tack-free

Example 4

A foam was produced in the same manner as in Example 2 starting from the following starting materials:

|         |                                                                                                                 |
|---------|-----------------------------------------------------------------------------------------------------------------|
| 33.01 g | of acrylic acid (0.46 mol) |
| 379.98 g | of a 40% strength triethanolammonium acrylate solution in water (0.69 mol) |
| 9.25 g | of guar flour |
| 1.85 g | of polyethylene glycol diacrylate of a polyethylene glycol of molecular weight 600 |
| 12.33 g | of a 15% strength aqueous solution of an adduct of 80 mol of ethylene oxide and 1 mol of a linear saturated $C_{16}C_{18}$ fatty alcohol |
| 72.83 g | of water |
| 4.63 g | of pentane |
| 20.97 g | of a 3% strength solution of 2,2'-azobis(2-amidino-propane) dihydrochloride in water |

Degree of neutralization: 60 mol %
Monomer foam density: 0.30
Polymer foam density: 0.40
Handle: dry, completely tack-free

Example 5

A foam was produced in the same manner as in Example 1 starting from the following starting materials:

|         |                                                                                                                 |
|---------|-----------------------------------------------------------------------------------------------------------------|
| 139.25 g | of acrylic acid (1.93 mol) |
| 39.51 g | of a 37.3% strength sodium acrylate solution in water (0.16 mol) |
| 9.25 g | of guar flour |
| 1.85 g | of polyethylene glycol diacrylate of a polyethylene glycol of molecular weight 500 |
| 58.58 g | of a 15% strength aqueous solution of an adduct of 80 mol of ethylene oxide and 1 mol of a linear saturated $C_{16}C_{18}$ fatty alcohol |
| 50.42 g | of water |
| 210.38 g | of triethanolamine (1.41 mol) |
| 4.63 g | of pentane |
| 20.97 g | of a 3% strength solution of 2,2'-azobis(2-amidino-propane) dihydrochloride in water |

Degree of neutralization: 75 mol %
Monomer foam density: 0.37 g/cm$^3$
Polymer foam density: 0.37 g/cm$^3$
Handle: dry, completely tack-free

Example 6

A foam was produced in the same manner as in Example 2 starting from the following starting materials:

|         |                                                                                                                 |
|---------|-----------------------------------------------------------------------------------------------------------------|
| 22.66 g | of acrylic acid (0.31 mol) |
| 405.84 g | of a 40% strength triethanolammonium acrylate solution in water (0.73 mol) |
| 9.25 g | of guar flour |
| 1.85 g | of polyethylene glycol diacrylate of a polyethylene glycol of molecular weight 650 |
| 12.33 g | of a 15% strength aqueous solution of an adduct of 80 mol of ethylene oxide and 1 mol of a linear saturated $C_{16}C_{18}$ fatty alcohol |
| 57.31 g | of water |
| 4.63 g | of pentane |
| 20.97 g | of a 3% strength solution of 2,2'-azobis(2-amidino-propane) dihydrochloride in water |

Degree of neutralization: 70 mol %
Monomer foam density: 0.32
Polymer foam density: 0.50
Handle: dry, completely tack-free

Example 7

The following components were mixed in a tube closed with a screw cap using a magnetic stirrer:

|         |                                                                                                                 |
|---------|-----------------------------------------------------------------------------------------------------------------|
| 79.89 g | of acrylic acid (1.11 mol) |
| 262.77 g | of a 40.0% strength triethanolammonium acrylate solution in water (0.48 mol) |
| 9.25 g | of guar flour |
| 1.85 g | of polyethylene glycol diacrylate of a polyethylene glycol of molecular weight 400 |
| 12.33 g | of a 15% strength aqueous solution of an adduct of 80 mol of ethylene oxide and 1 mol of a linear saturated $C_{16}C_{18}$ fatty alcohol |
| 143.16 g | of water |

The resulting homogeneous mixture was introduced into a closed 2 l flask with cooling jacket, into which carbon dioxide was passed from below. Two BOKU egg whisks connected via gears to an IKA RW28 W stirrer were inserted into the flask. The carbon dioxide stream was adjusted so that it bubbled at a rate of 100 l/h through the reaction mixture. The stirrer motor was initially adjusted to a speed of 200 rpm, and carbon dioxide was passed through the mixture for 20 min to remove dissolved oxygen. During this time, the internal temperature was cooled to 16° C. with the aid of the cooling jacket and a thermostat.

Subsequently, 4.63 g of pentane and 20.97 g of a 3% strength solution of 2,2'-azobis(2-amidinopropane) dihydrochloride in water were added, and the stirrer speed was increased to 735 rpm. The mixture was beaten at this speed for 3.5 min. After the end of the beating period, a fine-cell, free-flowing foam was obtained.

The resulting monomer foam was placed in a DIN A3-sized glass plate with edges 3 mm high and covered with a second glass plate. The foam sample was irradiated synchronously from both sides with two UV/VIS lamps (Höhnle UV 1000) for 4 minutes.

The resulting foam layer was sprayed with a 10% strength aqueous triethanolamine solution so that the degree of neutralization was increased from 30 mol % to 75 mol % and was then dusted on both sides with about 0.3 g of talc. The foam was completely dried in a vacuum oven at 70° C. To determine the properties, part of the foam was subsequently adjusted to a moisture content of 10% by spraying with water.
Degree of neutralization: 75 mol %
Monomer foam density: 0.34 g/cm$^3$
Polymer foam density: 0.39 g/cm$^3$
Handle: dry, completely tack-free Example 8

The following components were mixed in a tube closed with a screw cap using a magnetic stirrer:

| | |
|---|---|
| 112.86 g | of acrylic acid (1.57 mol) |
| 131.68 g | of a 37.3% strength sodium acrylate solution in water (0.52 mol) |
| 9.25 g | of guar flour |
| 1.85 g | of polyethylene glycol diacrylate of a polyethylene glycol of molecular weight 500 |
| 37.00 g | of a 15% strength aqueous solution of an adduct of 80 mol of ethylene oxide and 1 mol of a linear saturated $C_{16}C_{18}$ fatty alcohol |
| 28.40 g | of water |

The resulting homogeneous mixture was introduced into a closed 2 l flask with cooling jacket and dropping funnel, into which nitrogen was passed from below. Two BOKU egg whisks connected via gears to an IKA RW28 W stirrer were inserted into the flask. The nitrogen stream was adjusted so that it bubbled at a rate of 100 l/h through the reaction mixture. The stirrer motor was initially adjusted to a speed of 200 rpm, and nitrogen was passed through the mixture for 20 min to remove dissolved oxygen. During this time, 124.53 g of methyldiethanolamine (1.05 mol) were added dropwise with cooling so that a final temperature of 16° C. was reached.

Subsequently, 6.94 g of pentane and 20.97 g of a 3% strength solution of 2,2'-azobis(2-amidinopropane) dihydrochloride in water were added, and the stirrer speed was increased to 735 rpm. The mixture was beaten at this speed for 6 min. After the end of the beating period, a fine-cell, free-flowing foam was obtained.

The resulting monomer foam was introduced into a Teflon-coated aluminum mold which was 20 cm×20 cm in size and had a rim 3 mm high, and was covered with a glass plate. The mold was placed on a hotplate (Ceran 500) with a surface temperature of 115° C. for 2 min, then simultaneously irradiated from above with a UV/VIS lamp (Höhnle UV 2000) and further heated from below for 2 min, and finally left on the hotplate for 2 min without irradiation.

The resulting foam layer was dusted on both sides with about 0.3 g of talc and completely dried in a vacuum oven at 70° C. To determine the properties, part of the foam was subsequently adjusted to a moisture content of 10% by spraying with water.
Degree of neutralization: 75 mol %
Monomer foam density: 0.36 g/cm$^3$
Polymer foam density: 0.43 g/cm$^3$
Handle: dry, completely tack-free Example 9

A foam was produced in the same manner as in Example 1 starting from the following starting materials:

| | |
|---|---|
| 120.18 g | of acrylic acid (1.67 mol) |
| 105.13 g | of a 37.3% strength sodium acrylate solution in water (0.42 mol) |
| 12.60 g | of guar flour |
| 8.82 g | of polyethylene glycol diacrylate of a polyethylene glycol of molecular weight 600 |
| 58.78 g | of a 15% strength aqueous solution of an adduct of 80 mol of ethylene oxide and 1 mol of a linear saturated $C_{16}C_{18}$ fatty alcohol |
| 55.99 g | of water |
| 155.51 g | of triethanolamine (1.04 mol) |
| 4.63 g | of pentane |
| 20.99 g | of a 3% strength solution of 2,2'-azobis(2-amidinopropane) dihydrochloride in water |

After drying, the foam was adjusted to a moisture content of 10% by spraying with water.
Degree of neutralization: 70 mol %
Monomer foam density: 0.26 g/cm$^3$
Polymer foam density: 0.26 g/cm$^3$
Handle: dry, completely tack-free Example 10

A foam was produced in the same manner as in Example 1 starting from the following starting materials:

| | |
|---|---|
| 127.93 g | of acrylic acid (1.77 mol) |
| 93.43 g | of a 37.3% strength sodium acrylate solution in water (0.37 mol) |
| 12.60 g | of guar flour |
| 6.29 g | of polyethylene glycol diacrylate of a polyethylene glycol of molecular weight 400 |
| 58.78 g | of a 15% strength aqueous solution of an adduct of 80 mol of ethylene oxide and 1 mol of a linear saturated $C_{16}C_{18}$ fatty alcohol |
| 63.02 g | of water |
| 152.42 g | of triethanolamine (1.02 mol) |
| 4.63 g | of pentane |
| 20.99 g | of a 3% strength solution of 2,2'-azobis(2-amidinopropane) dihydrochloride in water |

After drying, the foam was adjusted to a moisture content of 10% by spraying with water.
Degree of neutralization: 65 mol %
Monomer foam density: 0.28 g/cm$^3$
Polymer foam density: 0.23 g/cm$^3$
Handle: dry, completely tack-free Example 11

A foam was produced in the same manner as in Example 1 starting from the following starting materials:

| | |
|---|---|
| 119.27 g | of acrylic acid (1.66 mol) |
| 46.37 g | of a 37.3% strength sodium acrylate solution in water (0.18 mol) |
| 12.60 g | of guar flour |
| 8.82 g | of polyethylene glycol diacrylate of a polyethylene glycol of molecular weight 400 |
| 58.78 g | of a 15% strength aqueous solution of an adduct of 80 mol of ethylene oxide and 1 mol of a linear saturated $C_{16}C_{18}$ fatty alcohol |
| 92.84 g | of water |
| 178.34 g | of triethanolamine (1.20 mol) |
| 4.63 g | of pentane |

| 20.99 g | of a 3% strength solution of 2,2'-azobis(2-amidino-propane) dihydrochloride in water |

After drying, the foam was adjusted to a moisture content of 10% by spraying with water.
Degree of neutralization: 75 mol %
Monomer foam density: 0.27 g/cm$^3$
Polymer foam density: 0.25 g/cm$^3$
Handle: dry, completely tack-free

Example 12

A foam was produced in the same manner as in Example 1 starting from the following starting materials:

| | |
|---|---|
| 120.44 g | of acrylic acid (1.95 mol) |
| 12.60 g | of guar flour |
| 8.81 g | of polyethylene glycol diacrylate of a polyethylene glycol of molecular weight 600 |
| 58.78 g | of a 15% strength aqueous solution of an adduct of 80 mol of ethylene oxide and 1 mol of a linear saturated $C_{16}C_{18}$ fatty alcohol |
| 121.60 g | of water |
| 174.46 g | of triethanolamine (1.17 mol) |
| 4.63 g | of pentane |
| 20.99 g | of a 3% strength solution of 2,2'-azobis(2-amidino-propane) dihydrochloride in water |

After drying, the foam was adjusted to a moisture content of 10% by spraying with water.
Degree of neutralization: 60 mol %
Monomer foam density: 0.27 g/cm$^3$
Polymer foam density: 0.23 g/cm$^3$
Handle: dry, completely tack-free

Comparative Example 1

The following components were mixed in a tube closed with a screw cap using a magnetic stirrer:

| | |
|---|---|
| 37.64 g | of acrylic acid (0.52 mol) |
| 395.08 g | of a 37.3% strength sodium acrylate solution in water (1.57 mol) |
| 9.25 g | of guar flour |
| 1.85 g | of polyethylene glycol diacrylate of a polyethylene glycol of molecular weight 400 |
| 58.58 g | of a 15% strength aqueous solution of an adduct of 80 mol of ethylene oxide and 1 mol of a linear saturated $C_{16}C_{18}$ fatty alcohol |
| 6.85 g | of water |

The resulting homogeneous mixture was introduced into a closed 2 l flask with cooling jacket, into which carbon dioxide was passed from below. Two BOKU egg whisks connected via gears to an IKA RW28 W stirrer were inserted into the flask. The carbon dioxide stream was adjusted so that it bubbled at a rate of 100 l/h through the reaction mixture. The stirrer motor was initially adjusted to a speed of 200 rpm, and carbon dioxide was passed through the mixture for 20 min to remove dissolved oxygen. During this time, the internal temperature was adjusted to 16° C. with the aid of the cooling jacket and a thermostat. Subsequently, 4.63 g of pentane and 20.97 g of a 3% strength solution of 2,2'-azobis(2-amidinopropane) dihydrochloride in water were added, and the stirrer speed was adjusted to 735 rpm. The mixture was beaten at this speed for 3.5 min. After the end of the beating period, a fine-cell, free-flowing foam was obtained.

The monomer foam was placed in a DIN A3-sized glass plate with edges 3 mm high and covered with a second glass plate. The foam sample was irradiated synchronously from both sides with two UV/VIS lamps (Höhnle UV 1000) for 4 minutes.

The resulting foam layer was completely dried in a vacuum oven at 70° C. and then adjusted to a moisture content of 25% by spraying with water.
Degree of neutralization: 75 mol %
Monomer foam density: 0.31 g/cm$^3$
Polymer foam density: 0.32 g/cm$^3$
Handle: moist, scarcely tacky

Comparative Example 2

A foam was produced starting from the following components by the same procedure as in Comparative Example 1:

| | |
|---|---|
| 83.51 g | of acrylic acid (1.16 mol) |
| 292.28 g | of a 37.3% strength sodium acrylate solution in water (1.16 mol) |
| 9.25 g | of guar flour |
| 1.85 g | of polyethylene glycol diacrylate of a polyethylene glycol of molecular weight 500 |
| 58.58 g | of a 15% strength aqueous solution of an adduct of 80 mol of ethylene oxide and 1 mol of a linear saturated $C_{16}C_{18}$ fatty alcohol |
| 69.55 g | of water |
| 4.63 g | of pentane |
| 20.97 g | of a 3% strength solution of 2,2'-azobis(2-amidino-propane) dihydrochloride in water |

Degree of neutralization: 50 mol %
Monomer foam density: 0.26 g/cm$^3$
Polymer foam density: 0.29 g/cm$^3$
Handle: moist, scarcely tacky

Comparative Example 3

A foam was produced starting from the following components by the same procedure as in Comparative Example 1:

| | |
|---|---|
| 116.90 g | of acrylic acid (1.62 mol) |
| 175.37 g | of a 37.3% strength sodium acrylate solution in water (0.70 mol) |
| 9.25 g | of guar flour |
| 6.48 g | of polyethylene glycol diacrylate of a polyethylene glycol of molecular weight 500 |
| 58.58 g | of a 15% strength aqueous solution of an adduct of 80 mol of ethylene oxide and 1 mol of a linear saturated $C_{16}C_{18}$ fatty alcohol |
| 144.79 g | of water |
| 4.63 g | of pentane |
| 20.97 g | of a 3% strength solution of 2,2'-azobis(2-amidino-propane) dihydrochloride in water |

Degree of neutralization: 30 mol %
Monomer foam density: 0.26 g/cm$^3$
Polymer foam density: 0.24 g/cm$^3$
Handle: moist, scarcely tacky Comparative Example 4 (In Accordance with JP-A-08073507)

A mixture was produced from the following components in a closed flask with stirrer and nitrogen introduction from below:

| | |
|---|---|
| 180.00 g | of acrylic acid (2.50 mol) |
| 74.50 g | of triethanolamine (0.50 mol) |
| 42.00 g | of KOH (0.50 mol) |
| 74.00 g | of water |
| 0.25 g | of trimethylolpropane triacrylate |
| 3.33 g | of a 15% strength aqueous solution of sodium peroxodisulfate |

A stream of nitrogen was passed at 100 l/h through the mixture for 20 min in order to remove the dissolved oxygen.

Then 2.50 g of a 0.5% strength solution of ascorbic acid in water were added, and the mixture obtained after homogenization was introduced between two teflon plates held at a distance of 1 mm by a rubber seal.

The teflon plates were placed in a waterbath at 50° C.

After the reaction was complete, a 1 mm-thick gel film with a water content of 23% was obtained. It was very tacky.

Comparative Example 5

A mixture was produced from the following components in a closed flask with stirrer and nitrogen introduction from below:

| | |
|---|---|
| 180.00 g | of acrylic acid (2.50 mol) |
| 186.50 g | of triethanolamine (1.25 mol) |
| 118.50 g | of water |
| 4.00 g | of trimethylolpropane triacrylate |
| 3.33 g | of a 15% strength aqueous solution of sodium peroxodisulfate |

A stream-of nitrogen was passed at 100 l/h through the mixture for 20 min in order to remove the dissolved oxygen.

Then 2.50 g of a 0.5% strength solution of ascorbic acid in water were added, and the mixture obtained after homogenization was introduced between two teflon plates held at a distance of 1 mm by a rubber seal.

The teflon plates were placed in a waterbath at 50° C.

The resulting gel sheet was completely dried in a vacuum oven at 70° C. and then sealed in a polyethylene bag with the amount of water necessary to adjust the residual moisture content of the gel to 10%. After a waiting period of 10 days, the gel layer was uniformly moistened.

Comparative Example 6 (In Accordance with JP-A-08073507)

A mixture was produced from the following components in a closed flask with stirrer and nitrogen introduction from below:

| | |
|---|---|
| 180.00 g | of acrylic acid (2.50 mol) |
| 149.00 g | of triethanolamine (1.00 mol) |
| 14.00 g | of KOH (0.25 mol) |
| 86.00 g | of water |
| 0.11 g | of trimethylolpropane triacrylate |
| 3.33 g | of a 15% strength aqueous solution of sodium peroxodisulfate |

A stream of nitrogen was passed at 100 l/h through the mixture for 20 min in order to remove the dissolved oxygen.

Then 2.50 g of a 0.5% strength solution of ascorbic acid in water were added, and the mixture obtained after homogenization was introduced between two Teflon plates held at a distance of 1 mm by a rubber seal.

The Teflon plates were placed in a waterbath at 50° C.

After the reaction was complete, a 1 mm-thick gel film with a water content of 21% was obtained. It was very tacky.

TABLE 1

Flexibility of the foams

| | | Composition [mol %] | | | | Flexibility after storage at a temperature/rel. humidity of | | | |
|---|---|---|---|---|---|---|---|---|---|
| Example | Amine | Ammonium acrylate | Na acrylate | Acrylic acid | Flexibility after drying | 20° C./32% | 20° C./20% | 20° C./15% | 55° C./20% |
| Comp 1 | — | 0 | 75 | 25 | rigid | rigid | rigid | rigid | rigid |
| Comp 2 | — | 0 | 50 | 50 | rigid | rigid | rigid | rigid | rigid |
| Comp 3 | — | 0 | 30 | 70 | rigid | rigid | rigid | rigid | rigid |
| 1 | TEA[a] | 45 | 30 | 25 | rigid | flexible | flexible | scarcely flexible | resilient |
| 2 | TEA[a] | 45 | 0 | 55 | resilient | flexible | flexible | resilient | flexible |
| 3 | TEA[a] | 60 | 15 | 25 | resilient | flexible | flexible | flexible | flexible |
| 4 | TEA[a] | 60 | 0 | 40 | flexible | flexible | flexible | flexible | flexible |
| 5 | TEA[a] | 67.4 | 7.6 | 25 | resilient | flexible | flexible | flexible | flexible |
| 6 | TEA[a] | 70 | 0 | 30 | flexible | flexible | flexible | flexible | flexible |
| 7 | TEA[a] | 75 | 0 | 25 | flexible | flexible | flexible | flexible | flexible |
| 8 | MDA[b] | 50 | 25 | 25 | rigid | flexible | flexible | — | — |

[a] TEA = Triethanolamine
[b] MDA = Methyldiethanolamine

Then 2.50 g of a 0.5% strength solution of ascorbic acid in water were added, and the mixture obtained after homog-

TABLE 2

Flexibility of the foams at low temperatures

| Example | Amine | Composition [mol %] Ammonium acrylate | Na acrylate | Acrylic acid | Flexibility after storage at a temperature of +20° C. | +2° C. | −15° C. |
|---|---|---|---|---|---|---|---|
| Comp 1 | — | 0 | 75 | 25 | rigid | rigid | rigid |
| Comp 2 | — | 0 | 50 | 50 | rigid | rigid | rigid |
| Comp 3 | — | 0 | 30 | 70 | rigid | rigid | rigid |
| 1 | TEA[a] | 45 | 30 | 25 | flexible | flexible | flexible |
| 2 | TEA[a] | 45 | 0 | 55 | flexible | flexible | flexible |
| 3 | TEA[a] | 60 | 15 | 25 | flexible | flexible | flexible |
| 4 | TEA[a] | 60 | 0 | 40 | flexible | flexible | flexible |
| 5 | TEA[a] | 67.4 | 7.6 | 25 | flexible | flexible | flexible |
| 6 | TEA[a] | 70 | 0 | 30 | flexible | flexible | flexible |
| 7 | TEA[a] | 75 | 0 | 25 | flexible | flexible | flexible |
| 8 | MDA[b] | 50 | 25 | 25 | flexible | flexible | resilient |

[a]TEA = Triethanolamine

TABLE 3

Absorption properties

| Example | Amine | Composition [mol %] Ammonium acrylate | Na acrylate or K acrylate | Acrylic acid | AS [g/g sec] | Absorption [g/g] | Moisture content [%] | Absorption at 100% solids content [g/g] |
|---|---|---|---|---|---|---|---|---|
| Comp 1 | — | — | 75 | 25 | 0.79 | 36.2 | 25 | 48.3 |
| Comp 2 | — | — | 50 | 50 | 1.29 | 37.4 | 25 | 49.8 |
| Comp 3 | — | — | 30 | 70 | 1.84 | 34.1 | 25 | 45.5 |
| Comp 4 | TEA[a] | 20 | 30 | 50 | <0.02 | 12.5[b]/12.8[c] | 23 | 16.2[b]/16.2[c] |
| Comp 5 | TEA[a] | 50 | — | 50 | <0.02 | 14.3[b]/24.3[c] | 10 | 18.8[b]/27.0[c] |
| Comp 6 | TEA[a] | 40 | 10 | 50 | <0.02 | 16.3[b]/35.1[c] | 21 | 20.6[b]/44.4[c] |
| 9 | TEA[a] | 50 | 20 | 30 | 2.91 | 51.7 | 10 | 57.4 |
| 10 | TEA[a] | 48 | 17 | 35 | 3.25 | 55.9 | 10 | 62.1 |
| 11 | TEA[a] | 65 | 10 | 25 | 3.17 | 49.8 | 10 | 55.3 |
| 12 | TEA[a] | 60 | 0 | 40 | 3.07 | 52.3 | 10 | 58.1 |

[a]TEA = Triethanolamine
[b]The absorption values were measured after a swelling time of 60 min
[c]The absorption values were measured after a swelling time of 18 h

We claim:

1. A water-absorbing, expanded, crosslinked polymer obtainable by
   (I) foaming a polymerizable aqueous mixture which comprises
      (a) monoethylenically unsaturated monomers which contain acidic groups and are optionally neutralized,
      (b) optionally other monoethylenically unsaturated monomers,
      (c) crosslinkers,
      (d) initiators,
      (e) 0.1–20% by weight of at least one surfactant,
      (f) optionally at least one solubilizer and
      (g) optionally thickeners, foam stabilizers, polymerization regulators, fillers and/or cell nucleating agents, where the foaming takes place by dispersing fine bubbles of a gas which is inert to free radicals into the polymerizable aqueous mixture, and
   (II) polymerizing the foamed mixture to form an expanded hydrogel and, where appropriate, adjusting the water content of the expanded polymer to 1–60% by weight, if at least 20 mol % of the monomers (a) which contain acidic groups have been neutralized with tertiary alkanolamines and/or the free acidic groups of the expanded hydrogel have been at least 20 mol % neutralized with at least one alkalolamine after the polymerization.

2. The water-absorbing, expanded, crosslinked polymer as claimed in claim 1, wherein at least 40 mol % of the monomers (a) which contain acidic groups are neutralized with tertiary alkanolamines.

3. The water-absorbing, expanded, crosslinked polymer as claimed in claim 1, wherein the acidic groups of the expanded hydrogels are at least 40 mol % neutralized with at least one alkanolamine, the neutralization taking place after the polymerization.

4. The water-absorbing, expanded, crosslinked polymer as claimed in claim 2, wherein the alkanolamines are selected from the group of triethanolamine, methyldiethanolamine, dimethylaminodiglycol, dimethylethanolamine and N,N,N',N'-tetra(hydroxyethyl)ethylenediamine.

5. A process for producing water-absorbing, expanded, crosslinked polymers, which entails foaming a polymerizable mixture of (a) monoethylenically unsaturated monomers which contain acidic groups and are optionally neutralized, (b) optionally other monoethylenically unsaturated monomers, (c) crosslinkers, (d) optionally at least one polymerization initiator, (e) 0.1–20% by weight of at least one surfactant, (f) optionally at least one solubilizer and (g) optionally thickeners, foam stabilizers, polymerization regulators, fillers and/or cell nucleating agents, in a first stage by dispersing fine bubbles of a gas which is inert to free radicals, and polymerizing the resulting foam in a second stage to form an expanded hydrogel, and, where appropriate, adjusting the water content of the expanded polymer to 1–60% by weight, wherein at least 20 mol % of the monomers (a) which contain acidic groups are neutralized with tertiary alkanolamines and/or the free acidic groups of the expanded hydrogel are at least 20 mol % neutralized with at least one alkalolamine after the polymerization.

6. The process as claimed in claim 5, wherein the alkanolaminesa are selected from the group of triethanolamine, methyldiethanolamine, dimethylaminodiglycol, dimethylethanolamine, ethanolamine and N,N,N',N'-tetra(hydroxyethyl)ethylenediamine.

7. The process as claimed in claim 5, wherein at least 40 mol % of the monomers (a) which contain acidic groups are neutralized with tertiary alkanolamines and/or the free acidic groups of the expanded hydrogel are at least 40 mol % neutralized with at least one alkalolamine after the polymerization.

8. A polymer obtained by the process of claim 5.

9. A method of making hygiene articles employed to absorb body fluids and dressing materials for covering wounds, comprising combining the crosslinked polymer as claimed in claim 1 with a material selected from the group consisting of high loft nonwovens, polypropylene nonwovens, polyester nonwovens, and chemically modified celluloses.

10. The polymer of claim 1, wherein the surfactant is nonionic, anionic, or cationic.

11. The polymer of claim 1, wherein the surfactant is the adduct of an alkylene oxide and an alcohol, an amine, a phenol, a naphthol, or a carboxylic acid.

12. The polymer of claim 1, wherein the surfactant is the adduct of an alkali metal or ammonium salt of sulfuric acid half esters of adducts of ethylene oxide with propylene oxide and fatty alcohols, and alkali metal or ammonium salts of alkylbenzene-sulfonic acid or of alkylphenol ether sulfates.

13. The polymer of claim 1, wherein the surfactant is the product, quaternized with dimethyl sulfate, of the reaction of 6.5 mol of ethylene oxide with 1 mol of oleylamine, distearyl-dimethylammonium chloride, lauryltrimethylammonium chloride or cetylpyridinium bromide, or the triethanolamine ester of stearic acid which is quaternized with dimethyl sulfate.

14. The polymer of claim 1, wherein the surfactant is an adduct of 80 mol of ethylene oxide and 1 mol of a linear saturated $C_{16}$–$C_{18}$ fatty alcohol.

15. The polymer of claim 1, wherein the crosslinker is a N,N'-methylenebisacrylamide, a polyethylene glycol diacrylate or a polyethylene glycol dimethacrylate.

16. The polymer of claim 1, wherein the crosslinker is a polyethylene glycol diacrylate of polyethylene glycol of molecular weight 400–650.

17. The polymer of claim 1, wherein the polymerization initiator is selected from the group consisting of peroxides, hydroperoxides, persulfates, azo compounds, and redox catalysts.

18. The polymer of claim 1, wherein the polymerization initiator is 2,2'-azobis(2-amidopropane) dihydrochloride.

19. A process for thickening water-based surface coatings or paints, comprising adding the polymer of claim 1 in powder form to a water-based surface coating wherein the polymer is in powder form with an average particle diameter of 150 $\mu$m to 5 mm.

* * * * *